United States Patent
Wahlstrand et al.

(10) Patent No.: US 8,509,920 B2
(45) Date of Patent: Aug. 13, 2013

(54) ELECTRODE ARRANGEMENTS FOR MEDICAL LEAD

(75) Inventors: Carl D. Wahlstrand, North Oaks, MN (US); Dale F. Seeley, Spring Park, MN (US); Gabriela C. Molnar, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/376,133

(22) PCT Filed: Jun. 21, 2010

(86) PCT No.: PCT/US2010/039294
§ 371 (c)(1),
(2), (4) Date: Dec. 2, 2011

(87) PCT Pub. No.: WO2010/148375
PCT Pub. Date: Dec. 23, 2010

(65) Prior Publication Data
US 2012/0095540 A1    Apr. 19, 2012

Related U.S. Application Data

(60) Provisional application No. 61/218,456, filed on Jun. 19, 2009.

(51) Int. Cl.
*A61N 1/04* (2006.01)
(52) U.S. Cl.
USPC .......................... 607/118; 607/116; 607/117
(58) Field of Classification Search
USPC ......................... 607/118, 116, 117
See application file for complete search history.

(56) References Cited

U.S. PATENT DOCUMENTS

| | | |
|---|---|---|
| 3,804,098 A | 4/1974 | Friedman |
| 4,774,952 A | 10/1988 | Smits |
| 5,843,148 A | 12/1998 | Gijsbers |
| 7,515,968 B2 | 4/2009 | Metzler et al. |
| 7,672,734 B2 | 3/2010 | Anderson |
| 7,769,472 B2 | 8/2010 | Gerber |
| 7,996,092 B2 | 8/2011 | Mrva et al. |
| 2001/0025192 A1* | 9/2001 | Gerber et al. ............ 607/117 |
| 2004/0117728 A1 | 6/2004 | Gromer |
| 2007/0027514 A1* | 2/2007 | Gerber .................... 607/116 |
| 2008/0027524 A1* | 1/2008 | Maschino et al. ....... 607/118 |

OTHER PUBLICATIONS

PCT/US10/039294: Search Report and Written Opinion dated Oct. 6, 2010.
PCT/US10/039297: Search Report and Written Opinion dated Oct. 6, 2010.
PCT/US10/039295: Search Report and Written Opinion dated Oct. 11, 2010.

* cited by examiner

*Primary Examiner* — Christopher D Koharski
*Assistant Examiner* — Michael Carey

(57) ABSTRACT

An implantable medical lead includes a lead body having a proximal portion having a longitudinal axis and an arcuate distal body portion extending in the direction of the longitudinal axis. The arcuate distal body portion has a concave surface. The lead includes a plurality of elongate electrodes disposed at the arcuate distal end portion of the lead body along the concave surface. The electrodes extend substantially parallel to the longitudinal axis of the lead body.

16 Claims, 4 Drawing Sheets

ELECTRODE ARRANGEMENTS FOR MEDICAL LEAD

RELATED APPLICATION

This application is a U.S. National Stage filing under 35 U.S.C. 371 of copending PCT Application Serial No. PCT/US2010/039294, filed Jun. 21, 2010, which claims the benefit of priority to U.S. provisional patent application No. 61/218,456, filed Jun. 19, 2009, both of which applications are incorporated herein by reference to the extent that they do not conflict with the present disclosure.

FIELD

This disclosure relates to implantable medical devices. More particularly, it relates to implantable medical leads.

BACKGROUND

Many implantable medical devices, such as neurostimulators, pacemakers and defibrillators, transmit electrical signals to provide therapy to a patient. Electrical signals generated by the devices may be delivered to tissue of a patient via electrodes disposed at a distal end portion of a medical lead.

Typically, nervous tissue is targeted by the electrical signals. However, broad targeting of a nerve can have undesired consequences. For example, if a nerve is targeted for treatment of pain, selective targeting of afferent fibers, as opposed to efferent fibers, would be desired to avoid undesired motor side effects. Accordingly, targeting selected fascicles of a nerve or a group of fascicles would be preferred over broad targeting of the nerve.

However, such selective targeting of nerve fascicles can be difficult, as the fascicles do not often run in a nerve through a straight line. A lead having electrode configurations capable of facilitating selective capture of desired fascicles of a nerve would be desirable.

SUMMARY

The present disclosure describes, among other things, leads having an elongate arcuate distal portion with electrodes disposed along the concave surface of the arcuate distal portion. The arcuate distal portion may be implanted such that it partially surrounds a nerve. One or more electrodes may be employed to selectively apply an electrical signal to a particular set of nerve fibers (such as part of a fascicle), fascicle, or group of fascicles, of the nerve, such as those fascicles that tend to carry afferent sensory information.

In various embodiments, an implantable medical lead includes a lead body having a proximal portion having a longitudinal axis and an arcuate distal body portion extending in the direction of the longitudinal axis. The arcuate distal body portion has a concave surface. The lead includes a plurality of elongate electrodes disposed at the arcuate distal end portion of the lead body along the concave surface. The electrodes extend substantially parallel to the longitudinal axis of the lead body. Such an arrangement of the lead body and electrodes may be advantageous for stimulation of selective fascicles of a nerve when the lead is implanted such that the arcuate distal portion is substantially parallel to the nerve and the electrodes face the nerve.

These and various other features and advantages will be apparent from a reading of the following detailed description.

Figure 1:
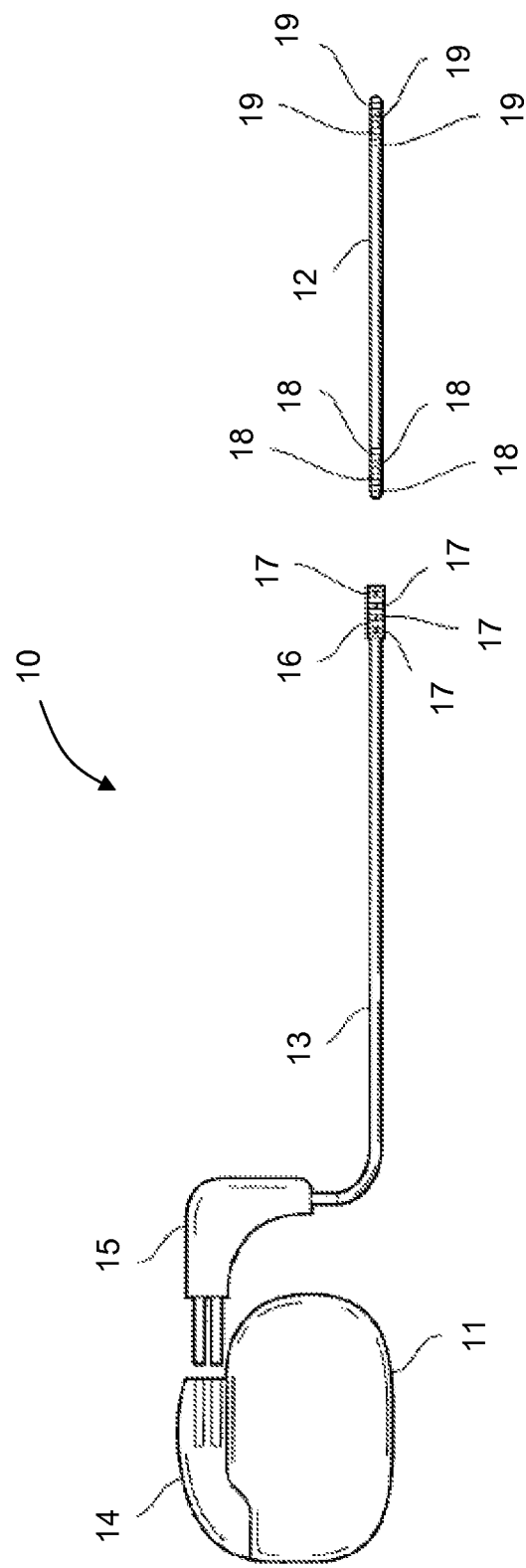
FIG. 1 is a schematic diagram of a side view of a representative stimulation system, illustrating a generic lead.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the apparatuses, systems and methods described herein. The following detailed description, therefore, is not to be taken in a limiting sense.

All scientific and technical terms used herein have meanings commonly used in the art unless otherwise specified. Any definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

The terms "left," "right," "front," "back," "top," "bottom," "over," "under," and the like, if any, are used herein for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. It will be further understood that directional terms, such as "longitudinal", "lateral", "transverse", and the like, when used with regard to a lead, are intended to have approximate practical meanings in view of the limp nature of implantable medical leads and the environment of use, rather than precise geometrical meanings.

The recitation herein of numerical ranges by endpoints includes all numbers subsumed within that range (e.g., 1 to 5 includes at least 1, 1.5, 2, 2.75, 3, 3.80, 4 and 5) and any range within that range.

As used herein, "representative," "exemplary," and the like are used in the context of "providing an example" and do not necessarily indicate that the example provided is superior to, or more particularly suited for the intended purpose than, other potential examples.

As used herein, "substantially" means to a great extent or degree. For example, "substantially" may be within 10% or within 5%; e.g., a substantially circular shape may be a shape that has a radius that varies less than 10% around the circumference. That is, the largest radius to a point on the circumference is not more than 10% greater than the smallest radius to a point on the circumference. By way of further example, an object that is substantially parallel to a first axis may be parallel to within 10%. That is, the longitudinal axis of the object is not more than 18 degrees (10% of 180 degrees is 18 degrees) from parallel with the first axis. By way of further example, an object that extends substantially the length of another object may extend between 90% and 110% of the length of the other object.

The present disclosure describes, among other things, leads having an elongate arcuate distal portion with electrodes disposed along the concave surface of the arcuate distal portion. The arcuate distal portion may be implanted such that it partially surrounds a nerve. One or more electrodes may be employed to selectively apply an electrical signal to a particular set of nerve fibers (such as part of a fascicle), fascicle, or group of fascicles, of the nerve, such as those fascicles that tend to carry afferent sensory information.

It will be understood, however, that the leads described herein may be used with any electrical medical device, such as an electrical signal generator for neuro, cardiac, or gastric stimulation or a monitoring device for any suitable purpose.

Referring to FIG. 1, a schematic side view of an embodiment of a representative system 10 is shown. System 10 includes an implantable electrical signal generator 11, a lead extension 13 and a lead 12. Implantable electrical signal generator 11 includes a connector header 14 configured to receive plug 15 at proximal end of lead extension 13 or other adaptor to operably couple lead 12 to electrical signal generator 11. The distal end portion of lead extension 13 includes a connector 16 configured to receive proximal end portion of lead 12. Connector 16 includes electrical contacts 17 configured to electrically couple extension 13 to lead 12 via electrical contacts 18 on the proximal end portion of lead 12. Electrodes 19 are present on distal end portion of lead 12 and are electrically coupled to electrical contacts 18, typically through conductors (not shown) within lead 12. In general, lead 12 may include any number of electrodes 19, e.g. one, two, three, four, five, six, seven, eight, sixteen or any other number. In some embodiments, each electrode 19 is electrically coupled to a discrete electrical contact 18, whereas in other embodiments, a set of electrodes 19 is electrically coupled to a discrete contact 18. While not shown, it will be understood that more than one lead 12 may be operably coupled to one electrical signal generator 11 or one extension 13 or that more than one extension 13 may be operably coupled to one electrical signal generator 11. It will be further understood that lead 12 may be coupled to electrical signal generator 11 without use of extension 13 or other adaptor.

The lead 12 depicted in FIG. 1 is shown for purposes of illustration of a lead in a system 10. The leads described in more detail herein have an elongate arcuate distal portion with electrodes disposed along the concave surface of the arcuate distal portion. In many embodiments, the electrodes are elongate and extend parallel to the longitudinal axis of the lead body. If the arcuate distal portion is implanted such that it partially surrounds a nerve, one or more electrodes that are located in proximity to a particular fascicle or group of fascicles may be selected to apply an electrical signal selectively to the desired fascicles.

Figure 2:
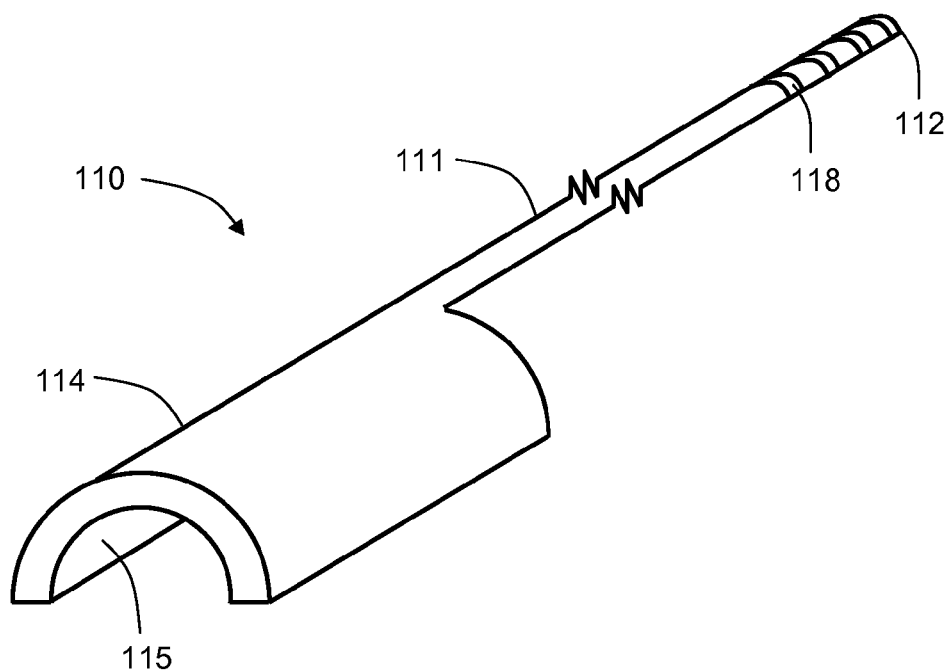
FIG. 2 is a schematic top perspective view of an embodiment of a lead having an arcuate distal end portion.
Figure 3:
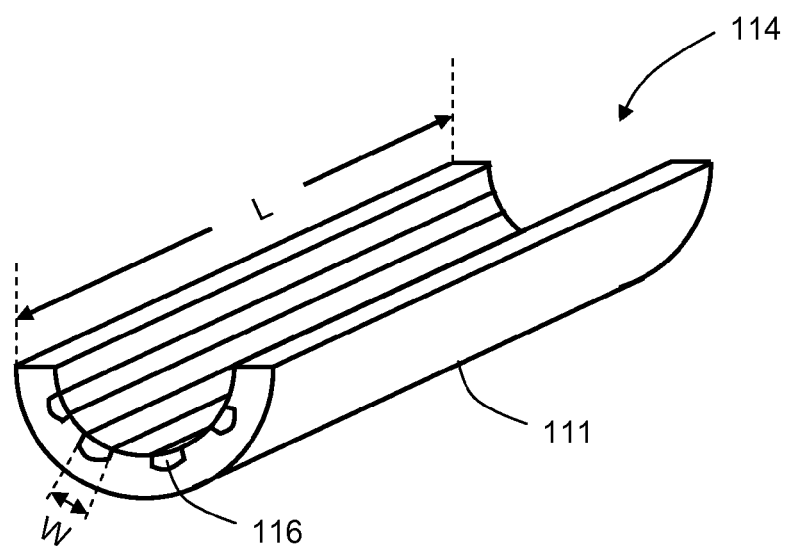
FIG. 3 is a schematic bottom perspective view of the arcuate distal end portion of FIG. 2.
Figure 4:
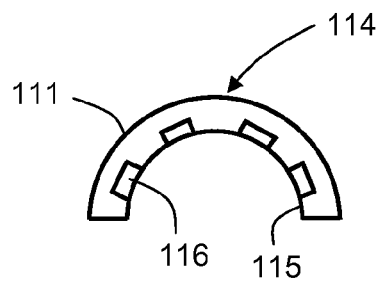
FIG. 4 is a schematic end view of the arcuate distal end portion of FIGS. 2 and 3.

FIGS. 2 through 8 illustrate a variety of leads having elongate longitudinal electrodes present on an arcuate distal end portion. As shown in FIGS. 2-4, the lead 110 may have a lead body 111 including a proximal portion having a proximal end 112 and an elongate distal arcuate portion 114. The proximal portion of the lead body has a longitudinal axis, and the arcuate distal portion 114 extends in the direction of the longitudinal axis. The arcuate distal end portion 114 has an enlarged surface area, as compared to that region of lead body 111 proximate to proximal end 112.

The distal end portion 114 is arcuate, and can be defined by a radius that is greater than 0; i.e., distal end portion is not flat or planar. Distal end portion 114 has the arcuate form in its unstressed state; i.e., no external force is acting on lead 110 or distal end portion 114 to hold distal end portion 114 in its arcuate state. Distal end portion 114 may be sufficiently flexible to allow distal end portion 114 to be flattened or further curved; however, distal end portion 114 will not maintain a flattened or planar configuration without an external force acting thereon.

In embodiment depicted in FIGS. 2-4, arcuate distal end portion 114 is a segment of a hollow cylinder having a semi-circular cross-section, having a constant radius. Additionally in this embodiment, arcuate distal end portion 114 is half of a hollow cylinder having a semi-circular cross-section, being an arc of 180 degrees. Arcuate distal end portion 114 is at least a 90 degree arc and typically less than a 270 degree arc, although some designs may have smaller or larger arcs.

Disposed along the inner or concave surface 115 of distal end portion 114 are a plurality of electrodes 116 have a length L in the longitudinal direction of lead 110 and a width W in the lateral direction (see, e.g., FIG. 3). In the embodiment illustrated in FIGS. 2-4, lead 110 has four electrodes 116, each electrically connected to a discrete contact 118 positioned at proximal end 112 of lead 110 (see, e.g., FIG. 2). Electrodes 116 have a generally rectangular cross-section, when taken laterally across lead 110. However, the electrode shape may vary between rectangular (as shown in FIG. 3), circular, elliptical, rectangular or square with rounded edges, leading to various possible cross-sectional shapes. In the depicted embodiment, electrodes 116 are recessed into body 111, so that the outer surface of electrode 116 is level with inner surface 115 of lead body 111.

The electrodes 116 depicted in FIGS. 2-4 extend substantially the length of the arcuate distal portion 114 and are arranged substantially parallel to the longitudinal axis of the proximal end portion of the lead body 111 (see, e.g., FIG. 2). In this manner, nearly any line drawn perpendicular to the longitudinal axis along the concave surface 115 of the distal end portion 114 would intersect the electrodes. Of course, the electrodes 116 may be arranged in any suitable manner.

Figure 5:
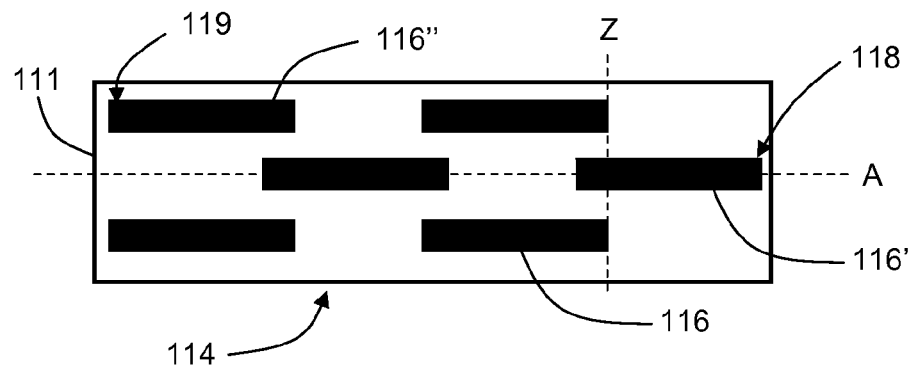
FIG. 5 is a schematic bottom view of an embodiment of a distal end portion of a lead.

For example and with reference to FIG. 5, which is a schematic view of a concave surface of an arcuate distal end portion 114 of a lead where the arcuate distal end portion 114 has been flattened, the elongate electrodes 116 may be staggered so that any line drawn perpendicular to the longitudinal axis A lead body along the concave surface of the arcuate distal end portion 114 will intersect at least one electrode 116, provided that the line is drawn between the most proximal end 118 of the most proximal electrode 116' and the most distal end 119 of the most distal electrode 116". Many of such lines would intersect more than one electrode 116. For example, line Z, which intersects the most proximal portion of electrode 116, also intersects electrode 116' between its proximal and distal end.

Figure 6:
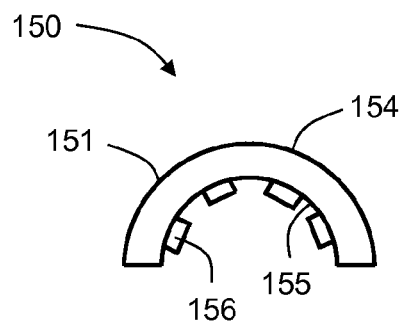
FIG. 6 is a schematic end view of an embodiment of an arcuate distal end portion of a lead.
Figure 7:
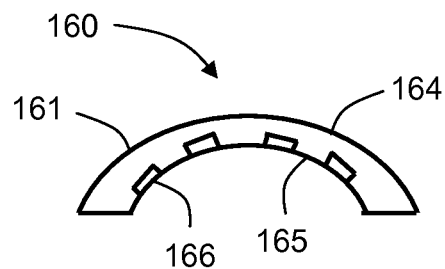
FIG. 7 is a schematic end view of an embodiment of an arcuate distal end portion of a lead.

FIGS. 6 and 7 illustrate end views of two alternate embodiments of leads having elongate arcuate distal end portions. In FIG. 6, lead 150 has a body 151 with an arcuate distal end portion 154 with four electrodes 156 radially positioned thereon. Arcuate distal end portion 154 is a semi-circle, having a constant radius, being an arc of about 180 degrees. Electrodes 156 are present on an inner concave surface 155 of lead body 151 and extend inwardly beyond the surface 155.

In FIG. 7, lead 160 has a body 161 with an arcuate distal end portion 164 with four electrodes 166 radially positioned thereon. Electrodes 166 are recessed into body 161, so that the outer surface of electrode 166 is level with an inner concave surface 165 of lead body 161. Of course, the electrodes may be disposed relative to the lead body so that they are recessed, flat or protrude from the concave surface of the distal end portion.

As further depicted in FIG. 7, the arcuate distal end portion 164 does not have a constant radius, but has a radius that changes along its arc. Distal end portion 164 is half of an ellipse, being an arc of about 180 degrees. Of course, the arc or the distal end portion 164 may be of any suitable shape, such as semi-circular, semi-elliptical, or the like. The Arc can extend to any suitable extent, such as 90 degrees or more or 180 degrees or more. In some embodiments, the arc extends between about 90 degrees and about 225 degrees, between about 135 degrees and 180 degrees, or between about 180 and about 270 degrees.

Figure 8:
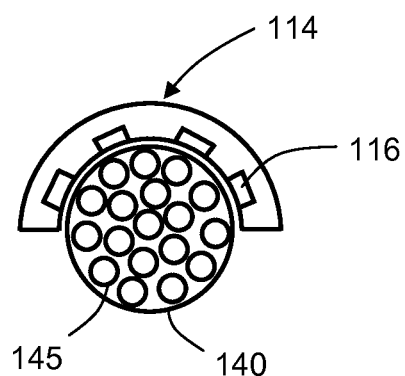
FIG. 8 is a schematic end view of an arcuate distal end portion of a lead positioned proximate a nerve to be stimulated.

FIG. 8 illustrates a benefit of having an arcuate distal end portion 114 with electrodes 116 thereon. The arcuate distal end portion 114 of the lead is illustrated positioned in close proximity to a nerve 140. The distal end portion 114 is implanted substantially parallel to the nerve such that the electrodes 116 face and at least partially surround the nerve 140. In some embodiments, nerve 140 is a median nerve having a substantially round configuration. Nerve 140 is composed of a plurality of fascicles 145, provided as a bundle within a sheath. With electrodes 116 of lead 110 arranged radially around nerve 140, selected fascicles 145 can be stimulated while unselected fascicles 145 are not stimulated, thus tailoring the pain relief and avoiding activating muscles distal to the point of stimulation. As fascicles 145 generally run parallel to the axis of the nerve 140, electrodes 116 positioned parallel to the nerve 116 have an advantage for selective stimulation relative to electrodes that may be positioned circumferentially around the nerve, as with cuff electrodes. Further selectivity may be achieved with staggered electrodes, such as those depicted in FIG. 5, or electrodes that do not extend the entire length of the arcuate distal region 114. That is, as fascicles 145 tend to follow a wandering path within a nerve 145, a greater number of shorter electrodes may be advantageous to a lesser number or longer electrodes, as the longer the electrode, the more likely it will be to capture an unintended fascicle, such as a fascicle carrying efferent fibers, when the fascicles do not follow a straight line path. In contrast, if the lead is placed in a location where fascicles do follow a substantially straight linear path, aligned electrodes may be desirable.

Regardless of the electrode configuration of the lead, one or more electrodes may be selected for purposes of applying an electrical signal to a nerve. Preferably, the electrodes are selected to apply the electrical signal selectively to a particular fascicle or group of fascicles, such as a fascicle carrying afferent fibers.

The leads described herein may be used for any suitable purpose, such as treatment of chronic pain associated with a peripheral nerve, such as pain associated with carpal tunnel syndrome or with hernia operations. Carpal tunnel results from the chronic entrapment of the median nerve, which is composed of many different fascicles, which typically do not remain in the same arrangement throughout the length of the nerve. Chronic pain can result if the entrapment is not relieved or if surgical intervention to relieve the entrapment causes scar tissue or mild neuropathy. Herniorrhaphy is a surgical procedure for correcting a hernia. Hernias can occur in the abdomen, groin, and at the site of a previous surgery. There are several known repairs for hernias, and chronic pain can result from all types of repair procedures. This chronic post herniorrhaphy pain can result from damage to and entrapment of nerves innervating the surgical region. The formation of neuromas, scar tissue, and misplaced mesh may also be a cause for chronic pain. The affected nerves can include the ilioinguial, the iliohypogastric and the lateral femoral cutaneous. Leads having an arcuate distal end as described herein, when used as part of system 10 of FIG. 1, may be used to effectively treat chronic pain conditions. These systems are highly effective, easy to implant, safe, reliable, and easy to maintain long-term.

It will be understood that electrical signal parameters may be varied as desired for treating pain. Typically, the frequency, amplitude or pulse width of an electrical signal may be varied. An electrical signal having any suitable frequency for treating pain may be used to treat pain as described herein. For example, an electrical signal may have a frequency of about 0.5 Hz to 500 Hz (e.g., about 5 Hz to 250 Hz or about 10 Hz to 50 Hz). For example, the amplitude may be about 0.1 volts to 50 volts (e.g., about 0.5 volts to 20 volts or about 1 volt to 10 volts); for devices that the amps rather than voltage, one skilled in electronics understands the conversion from volts to amps for stimulation devices. An electrical signal may have any suitable pulse width. For example, the signal may have a pulse width of 10 microseconds to 5000 microseconds (e.g., about 100 microseconds to 1000 microseconds or about 180 microseconds to 450 microseconds). For some patients with some devices, the determination of the optimal location and parameters for stimulation occurs within days, for others, within hours or minutes.

Regardless of the use of the leads described herein, some features or aspects of some embodiments of leads having arcuate distal end portions are provided below. Leads having an arcuate distal end portion may be implanted into the patient either in their curved, unstressed state, or may be manipulated to a different shape during implantation and then returned to their unstressed state during use. For example, distal end portion may be wrapped tighter to allow insertion via a smaller introducer. Alternately, distal end portion may be deployed in a flattened state and then released. Shape retaining polymeric materials are particularly suited for distal end portions that are flattenable or wrappable.

The electrodes described herein have an overall elongated shape with an aspect ratio L:W (i.e., length in the longitudinal direction:width in the lateral direction) of at least 2:1; e.g., at least 4:1, at least 5:1 or at least 10:1. That is, the dimension of the electrode in the longitudinal direction is greater than, and in some embodiments, significantly greater than the dimension in the lateral direction. While depicted herein as rectangular, the exposed surface area of an elongate electrode may be any shape, such as oval or elliptical.

The active length of the electrodes, in the longitudinal direction, is at least about 0.5 mm and in some embodiments at least about 1 mm. The active length may be, for example, about 1 mm to about 50 mm (5 cm), in some embodiments about 2 mm to about 20 mm (2 cm). Particular example lengths include 2 mm, 5 mm, 10 mm (1 cm), 15 mm (1.5 cm). For some embodiments, electrode lengths of 3.8 mm (about 0.15 inch) or 2.54 mm (0.1 inch) are preferred. The overall length of the electrode, in the longitudinal direction, is, in some embodiments, at least 0.5 mm and in some embodiments at least about 1 mm.

In some embodiments, the width of the electrodes, in the lateral direction, is about 0.1 mm to about 5 mm, in other embodiments, about 0.5 mm to about 2 mm. For some embodiments, electrode widths of about 0.25 mm (about 0.0.1 inch) or about 0.5 mm (about 0.020 inch) are preferred.

The active surface areas of electrodes may be about 2 mm$^2$ to about 100 mm$^2$ (1 cm$^2$), about 20 mm$^2$ to about 50 mm$^2$.

Inter-electrode distances are often about 3 mm, but other inter-electrode distances may be used such as about 1 mm, about 2 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, and about 30 mm. Inter-electrode distances refers to the lateral distance between electrodes (edge to edge) or to the longitudinal distance between electrodes (edge to edge).

The electrode arrangement may be in-line, staggered, or any other suitable configuration. Any suitable number of electrodes may be present on the arcuate distal end of the lead. For example, the arcuate distal end portion may have 4, 8, 10, 16 or more electrodes. By way of example, the number of electrodes along the lateral direction may be one or more, and may be 3, 4, or 5. By way of further example, the number of electrodes along the longitudinal direction may be one or more, and may be 2, 3, or 4. A large number of closely spaced electrodes will provide further options to selectively activate nerve fibers within a fascicle, fascicles or groups of fascicles.

Polyurethane is a suitable material for forming the lead body, although other materials such as silicone may be used. Electrical conductors extending between the proximal end and the distal end portions for supplying electrical current to the electrodes may be formed of coiled, braided or stranded wires comprising an electrical conductive material, e.g., MP35N or a platinum-iridium alloy. The electrodes are preferably formed of platinum, although other metals and metal alloys, such as gold or stainless steel, can be used. In some embodiments, non-metallic yet electrically conductive materials may be used as the electrodes and/or electrical conductors.

In various embodiments, a lead has a diameter in its proximal portion of about 5 mm or less, such as about 2 mm or less or about 1.5 mm. The arcuate distal end portion of a lead may have any suitable lateral dimension. For example, the arcuate distal end portion may have a lateral dimension of up to about 10 mm, but in most embodiments is less than about 5 mm.

One of skill in the art will understand that components described herein regarding a given embodiment or set of embodiments may readily be omitted, substituted, or added from, with, or to components of other embodiments or sets of embodiments, as appropriate or desirable.

Thus, embodiments of ELECTRODE ARRANGEMENTS FOR MEDICAL LEAD are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical lead comprising: a lead body including (i) a proximal portion having a longitudinal axis, and (ii) an arcuate distal portion extending in the direction of the longitudinal axis, the arcuate distal portion having a concave surface; and
   a plurality of elongate electrodes disposed at the arcuate distal portion of the lead body along the concave surface, the electrodes extending substantially parallel to the longitudinal axis of the lead body,
   wherein the plurality of electrodes comprises a first electrode having a distal end and a proximal end and a second electrode having a distal end and a proximal end, wherein a line perpendicular to the longitudinal axis across the concave surface intersects the first electrode at the proximal end and intersects the second electrode between the proximal and distal ends,
   wherein each of the plurality of electrodes has an aspect ratio of its longitudinal length to its lateral width of at least 4:1.

2. An implantable medical lead according to claim 1, wherein the arcuate distal portion has a length and wherein at least one of the plurality of electrodes extends substantially the length of the arcuate distal portion.

3. An implantable medical lead according to claim 1, wherein the arcuate distal portion has a length and wherein each of the plurality of electrodes extends the length of the arcuate distal portion.

4. An implantable medical lead according to claim 1, wherein each of the plurality of electrodes has an aspect ratio of its longitudinal length to its lateral width of at least 5:1.

5. An implantable medical lead according to claim 1, wherein the plurality of electrodes comprises at least four electrodes.

6. An implantable medical lead according to claim 1, wherein the concave surface of the arcuate distal end portion is defined by a segment of a cylinder having a substantially semi-circular cross section along its length.

7. An implantable medical lead according to claim 6, wherein the segment of the cylinder extends 90 degrees or more around its circular cross section.

8. An implantable medical lead according to claim 6, wherein the segment of the cylinder extends 180 degrees or more around its circular cross section.

9. An implantable medical lead according to claim 1, each of the plurality of electrodes has a length of at least 2 mm.

10. An implantable medical lead according to claim 1, each of the plurality of electrodes has a length of at least 2.5 mm.

11. An implantable medical lead according to claim 1, wherein the plurality of electrodes consists of four or eight electrodes.

12. A method for applying an electrical signal to a nerve, comprising:
    implanting a medical lead according to claim 1 in proximity to the nerve such that the arcuate distal portion is substantially parallel to a portion of the nerve and the electrodes face the nerve; and
    applying an electrical signal to the nerve via one or more of the plurality of electrodes.

13. A method according to claim 12, wherein the nerve is a peripheral nerve.

14. A method according to claim 12, further comprising identifying an electrode or combination of electrodes of the plurality of electrodes that selectively applies the electrical signal to afferent fibers within the nerve.

15. A method according to claim 12, wherein the nerve is a nerve of a patient suffering from pain.

16. A method according to claim 15, wherein the electrical signal is applied for treating the pain.

\* \* \* \* \*